(12) United States Patent
Weinstein et al.

(10) Patent No.: US 8,765,678 B2
(45) Date of Patent: Jul. 1, 2014

(54) INHIBITION OF THE RENIN-ANGIOTENSIN SYSTEM FOR THE TREATMENT OF RENAL, VASCULAR AND CARTILAGE PATHOLOGY

(75) Inventors: Talia Weinstein, Tel-Aviv (IL); Uzi Gafter, Petach-Tikva (IL); Zvi Nevo, Herzlia (IL); Dror Robinson, Doar-Na Shimshon (IL); Zoharia Evron, Hod-HaSharon (IL)

(73) Assignee: Mor Research Applications Ltd., Tel-Aviv (IL)

( * ) Notice: Subject to any disclaimer, the term of this patent is extended or adjusted under 35 U.S.C. 154(b) by 1101 days.

(21) Appl. No.: 11/989,476

(22) PCT Filed: Jul. 27, 2006

(86) PCT No.: PCT/IL2006/000871
§ 371 (c)(1),
(2), (4) Date: Feb. 11, 2009

(87) PCT Pub. No.: WO2007/013078
PCT Pub. Date: Feb. 1, 2007

(65) Prior Publication Data
US 2009/0192119 A1    Jul. 30, 2009

Related U.S. Application Data

(60) Provisional application No. 60/754,181, filed on Jul. 27, 2005.

(51) Int. Cl.
*A61K 38/00* (2006.01)

(52) U.S. Cl.
USPC ........ 514/16.6; 514/16.8; 514/863; 435/7.71; 930/250

(58) Field of Classification Search
USPC ......... 514/16.6, 16.8, 863; 435/7.71; 930/250
See application file for complete search history.

(56) References Cited

U.S. PATENT DOCUMENTS

| 5,641,747 | A * | 6/1997 | Popoff et al. ................ 514/16.9 |
| 2003/0040509 | A1* | 2/2003 | Moskowitz ................... 514/171 |
| 2003/0064933 | A1* | 4/2003 | Li et al. ........................... 514/19 |
| 2005/0187163 | A1 | 8/2005 | Rodgers et al. | |

FOREIGN PATENT DOCUMENTS

| EP | 0970694 A2 * | 1/2000 |
| EP | 0970694 B1 * | 7/2006 |
| EP | 1806137 | 7/2007 |
| WO | WO 2006/046528 | 5/2006 |
| WO | WO 2007/013078 | 2/2007 |

OTHER PUBLICATIONS

Office Action Dated Sep. 5, 2011 From the Israel Patent Office Re.: Application No. 188893 and Its Translation Into English.
International Preliminary Report on Patentability Dated Feb. 7, 2008 From the International Bureau of WIPO Re.: Application No. PCT/IL2006/000871.
International Search Report Dated Dec. 28, 2006 From International Searching Authority Re.: Application No. PCT/IL2006/000871.
Response Dated Jul. 22, 2010 to Office Action of Mar. 22, 2010 From the Israel Patent Office Re.: Application No. 188893.
Office Action Dated Mar. 22, 2010 From the Israel Patent Office Re.: Application No. 188893 and Its Translation Into English.
Bird et al. "A Clinical and Biochemical Assessment of a Nonthiol (Pentopril; CGS-13945) in Active Rheumatoid Arthritis", Journal of Rheumatology, 17(5): 603-608, May 1990. Abstract.
Martin et al. "Captopril: A New Treatment for Rheumatoid Arthritis?", The Lancet, 1(8390): 1325-1328, Jun. 16, 1984. Abstract.
Dalbeth et al. "The Non-Thiol Angiotensin-Converting Enzyme Inhibitor Quinapril Suppresses Inflammatory Arthritis", Rheumatology, XP009075369, 44: 24-31, 2005. p. 29, col. 1, § 2—p. 30, col. 1, § 2.
Jubb "Oral and Intra-Articular Remedies: Review of Papers Published From Mar. 2001 to Feb. 2002", Current Opinion in Rheumatology, XP009075433, 14: 597-602, 2002.
Shimizu-Hirota et al. "Regulation of Vascular Proteoglycan Synthesis by Angiotensin II Type 1 and Type 2 Receptors", Journal of the American Society of Nephrology, XP002409133, 12(12): 2609-2615, 2001. Abstract.
Wapstra et al. "ACE-Inhibition Restores Loss of Heparan Sulfate (IIS) in the Glomerular Basement Membrane (GBM) of Rats With Established Adriamycin (ADM) Nephrosis", Journal of the American Society of Nephrology, Immunology/Pathology, XP009075425, p. 797, Abstract 28P, 1994. Abstract.
Weinstein et al. "Enalapril Modifies Glycosaminoglycan (GAG) Expression in the Glomerular Basement Membrane (GMB) of Rats With Puromycin (PAN) Nephrosis", Journal of the American Society of Nephrology, XP009075424, 10: 564A, Abstract A2854, 1999. Abstract.
Translation of Notice of Reason for Rejection Dated Jan. 6, 2012 From the Japanese Patent Office Re. Application No. 2008-523539.
Translation of Notice of Reason for Rejection Dated May 22, 2012 From the Japanese Patent Office Re. Application No. 2008-523539.
Requisition by the Examiner Dated Apr. 18, 2013 From the Canadian Intellectual Property Office Re. Application No. 2,616,150.
Office Action Dated Mar. 10, 2013 From the Israel Patent Office Re.: Application No. 188893 and Its Translation Into English.
Communication Pursuant to Article 94(3) EPC Dated Apr. 5, 2013 From the European Patent Office Re. Application No. 06766186.8.

* cited by examiner

*Primary Examiner* — Patrick Lewis
*Assistant Examiner* — Everett White

(57) ABSTRACT

A method of treating a disease or condition in which up-regulating GAGs is therapeutically beneficial is disclosed, in particular osteoarthritis and skin diseases. The method comprises locally administering to a subject a therapeutically effective amount of an agent capable of down-regulating activity or expression of a component of the renin-angiotensin system.

7 Claims, 5 Drawing Sheets

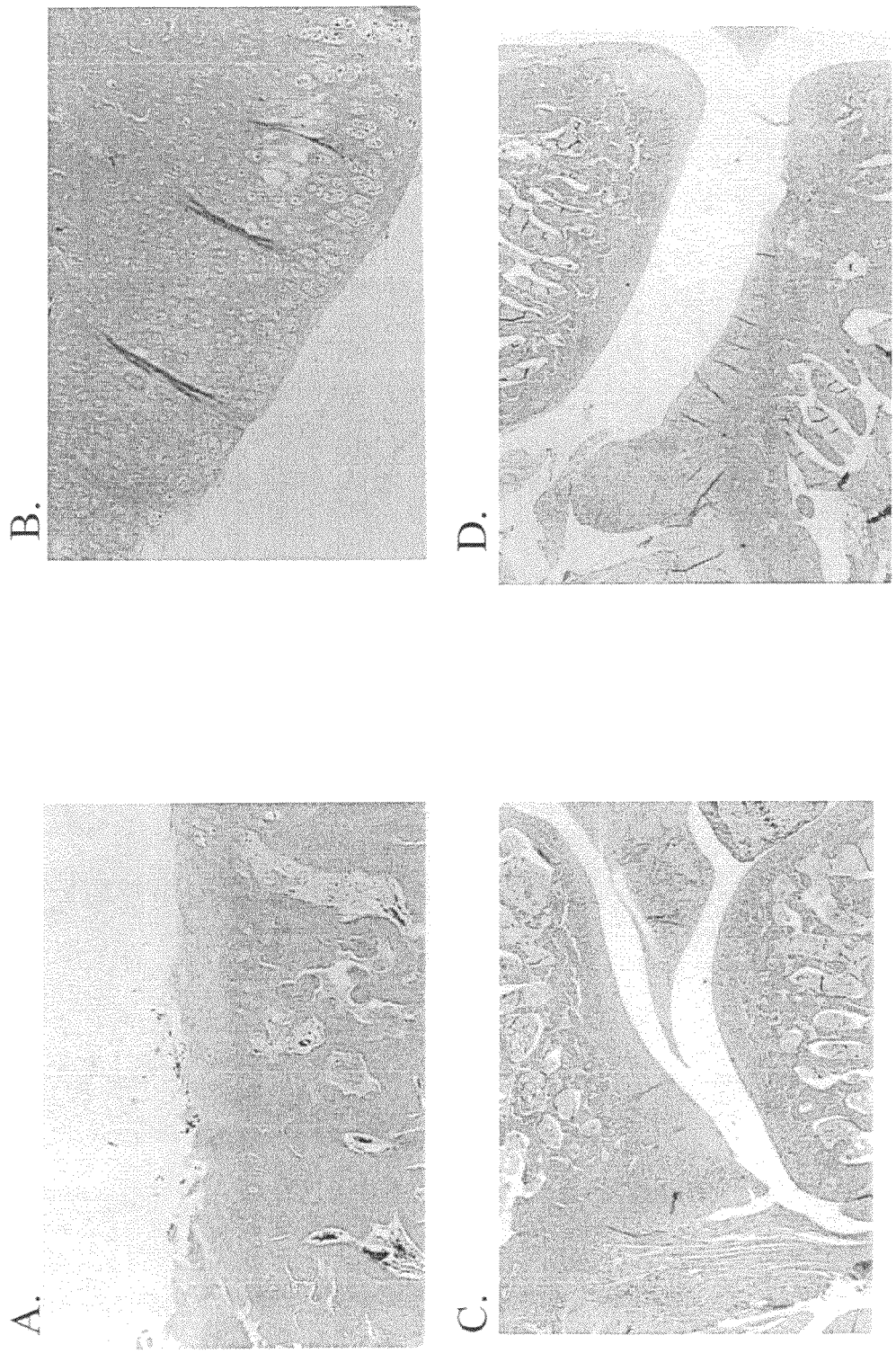
FIGs. 5A-D

INHIBITION OF THE RENIN-ANGIOTENSIN SYSTEM FOR THE TREATMENT OF RENAL, VASCULAR AND CARTILAGE PATHOLOGY

RELATED APPLICATIONS

This Application is a National Phase of PCT Patent Application No. PCT/IL2006/000871 having International Filing Date of Jul. 27, 2006, which claims the benefit of U.S. Provisional Patent Application No. 60/754,181 filed on Jul. 27, 2005. The contents of the above Applications are all incorporated herein by reference.

FIELD AND BACKGROUND OF THE INVENTION

The present invention relates to methods for treating conditions in which up-regulation of GAGs would be therapeutically beneficial and more specifically for treating such conditions by inhibiting the renin-angiotensin system.

It is known that glycosaminoglycans (GAGs) are the most abundant heteropolysaccharides in the body. They are essentially long unbranched polysaccharides comprising a repeating disaccharide unit which in turn comprise one of two modified sugars N-acetylgalactosamine (GalNAc) or N-acetylglucosamine (GlcNAc) and a uronic acid such as glucuronate or iduronate. GAGs are located primarily on the cell surface or in the extracellular matrix (ECM). Specific GAGs of physiological significance include hyaluronic acid, dermatan sulfate, chondroitin sulfate, heparin, heparan sulfate, and keratan sulfate.

The majority of GAGs in the body are linked to core proteins, forming proteoglycans (also referred to as mucopolysaccharides). The GAGs extend perpendicularly from the core in a brush-like, structure. The linkage of GAGs to the protein core involves a specific trisaccharide composed of two galactose residues and a xylose residue (GAG-Gal-GalXyl-O—$CH_2$-protein).

The high negative charge associated with GAGs, as well as their extended conformation imparts high viscosity to the ECM. Due to the low compressibility of GAGs, their presence in joint synovial fluid is essential. At the same time, their rigidity provides structural integrity to cells and provides passageways between cells, allowing for cell migration.

Because of the many vital body functions performed by proteoglycans in general and GAGs in particular, a deficiency in their production or their rapid degradation is associated with a wide range of disorders. In addition, many disorders have been shown to benefit by an increase in GAGs.

Osteoarthritis is the most common form of arthritis affecting over 20 million people in the United States alone. The incidence of osteoarthritis increases with age. The disease involves progressive deterioration of articular cartilage with minimal inflammation [Schoenherr et al. in Small Animal Clinical Nutrition 4.sup.th Ed., Hand et al. Eds., Walsworth Publishing Company, Marceline, Mo., 2000, 907-921; Hedbom et al., Cell Mol. Life. Sci 59:45-53, 2002; Pool, Front Biosci 4:D662-70, 1999].

Articular cartilage comprises chondrocytes (approximately 5%) and extracellular matrix (approximately 95%). The chondrocytes are important in the control of matrix turnover through production of collagen, proteoglycans and GAGs and enzymes for cartilage metabolism. The functional integrity of articular cartilage is determined by a balance between chondrocyte biosynthesis of extracellular matrix and its degradation.

Chondroitin sulfate is the predominant GAG found in articular cartilage. Together with its associated core protein, chondroitin sulfate has been shown to be reduced in various forms of arthritis including osteoarthritis as well as rheumatoid arthritis, leading to a decrease in cartilage thickness and stiffness [Altman R D, et al., Arthritis Rheum 16:179, 1973; Jasin H E, Dingle J T, J Clin Invest 68:571-581, 1981].

Standard drug therapy for the treatment of arthritis suppresses pain and inflammation, primarily through the use of non steroidal anti-inflammatory drugs (NSAIDS). However, these drugs also promote progression of the disease process by inhibiting GAG synthesis and cartilage repair. Therefore several attempts have been made to affect GAG and proteoglycan constituents of articular cartilage directly, using various approaches.

One such approach is the administration of glucosamine sulfate which is an essential component in GAG synthesis. Several human studies have shown a modest decrease in symptoms of osteoarthritis with the administration of glucosamine sulfate using oral or intraarticular injections [Reichelt A et al., Arzneimittelforschung 44:75-80, 1994; Reginster J Y, et al., Lancet 357:251-256, 2001; Vajaradul Y, Clin Ther 3:336-343, 1981]. A meta-analysis of the six best-designed trials found a small to moderate beneficial effect of glucosamine on pain [McAlindon T E, JAMA 15:1469-1675, 2000].

Another approach is the administration of chondroitin sulfate. A meta-analysis in 2003 evaluated eight trials that involved 755 patients with osteoarthritis of the knee who were assigned to receive chondroitin sulfate or placebo [Richy F, Arch Intern Med 163:1514-1522, 2003]. In terms of benefit, the likelihood of responding to chondroitin sulfate was significantly increased compared to placebo. However, there is limited information about the long-term effects of these supplements and their potential interactions. In addition, chondroitin and glucosamine usually require administration for many months before any benefit is felt.

Several genetically inherited diseases, for example the lysosomal storage diseases, result from defects in the lysosomal enzymes responsible for the metabolism of complex membrane-associated GAGs. These specific diseases, termed mucopolysaccharidoses (MPS) in reference to the earlier term, mucopolysaccharide, used for glycosaminoglycans, lead to an accumulation of defective GAGs within cells that fail to be secreted or degraded. There are at least 14 known types of lysosomal storage diseases that affect GAG metabolism; some of the more commonly encountered examples are Hurler's syndrome, Hunter's syndrome, Sanfilippo syndrome, Maroteaux-Lamy syndrome and Morquio's syndrome. All of these disorders, except for Hunter's syndrome, are inherited in an autosomal recessive manner.

Several approaches are being used or pursued for the treatment of MPS, most of which focus on gene therapy or enzyme replacement therapy for use alone in disease management. Additionally, researchers have identified a number of small molecules for the management of MPS. However, none of these approaches have shown full therapeutic efficacy.

Cystic fibrosis is another example of a disease which is associated with an increase in GAGs. Cystic fibrosis (CF) patients develop chronic lung infections associated with airway obstruction by viscous and insoluble mucus secretions. Chondroitin sulfate proteoglycans (CSPG) have been shown to contribute to the insolubility of CF sputum and treatment with chondroitinase was shown to ameliorate this effect [Khatri et al., Pediatr Res. 2003 April; 53(4):619-27].

There is thus a widely recognized need for, and it would be highly advantageous to have, novel therapeutic modalities for treating disorders associated with an under- or over-production of GAGs, which are devoid of the above limitations.

Angiotensin converting enzyme (ACE) is a metallopeptidase that participates in tissue regulatory peptide systems involving angiotensin II (AII) and bradykinin. ACE catalyses the formation of AII from its inactive precursor, angiotensin I, which itself is generated by cleavage of angiotensinogen by the protease renin. AII exerts its biologic effects via specific, cell surface receptors, of which two major subtypes, named AT1 and AT2 receptors have been identified in humans. AII is a potent vasoconstrictor, and can stimulate angiogenesis, fibroblast proliferation, and growth factor expression, each mediated by AT1 receptors [Timmermans P B, Pharmacol Review, 45:205-251, 1993]. Furthermore, ACE inhibitors (ACE-I) and AT1 receptor antagonists (ARB) inhibit these effects.

ACE inhibitors and ARBs are typically prescribed for the management of heart failure, hypertension and myocardial infarction. They are also considered as the standard of care for preserving renal function in chronic renal disease and in renal disorders associated with proteinuria. The precise mechanism of renoprotection associated with these agents is still not defined.

While researching the mechanism involved in the therapeutic effect ACE inhibitors and ARBs have on the pathogenesis of proteinuria, the present inventors unexpectedly discovered that inhibition of the renin-angiotensin system up-regulates GAGs. Thus, the use of ACE inhibitors and ARBs in the treatment of pathologies that would benefit from an up-regulation of GAGs is proposed herein. Particularly of interest is the local administration of such agents for the treatment of diseases associated with a low level of GAGs in the cartilage.

U.S. Pat. App. No. 20030078190 teaches the treatment of a wide range of disorders including rheumatoid arthritis (RA) and lupus erythematosus using ARBs optionally in combination with ACE-I inhibitors.

U.S. Pat. App. No. 20030040509 relates to the use of ACE inhibitors for the treatment of diseases associated with a reduced level of Angiotensin II. Included in their list of diseases are also those that are associated with a low level of GAGs.

Contrary to the present invention, both of these patent applications do not teach local administration of the renin-angiotensin modulating agent. Furthermore, therapeutic efficacy was shown only for cardiovascular disorders such as hypertension chronic heart failure and renal disorders such as proteinuria and chronic renal disease and not for cartilage, skin or lysosomal storage disorders.

There have been several small open-labelled trials of ACE inhibitors in patients with rheumatoid arthritis, with variable results [Martin M F et al., Lancet 1984; 1:1325-8; Bird H A et al., J. Rheumatol 1990; 17:603-8] using the ACE inhibitor captopril. The clinical benefits of captopril were attributed to structural similarities with penicillamine due to its thiol residue [Martin M F et al., Lancet 1984; 1: 1325-8]. In a later study ACE-I quinapril was shown to suppress inflammatory arthritis in mice [Dalbeth et al., Rheumatology 44:24-31, 2004]. The ARB candesartan had a similar inhibitory effect on disease activity as well. In all these studies, local administration of the renin angiotensin system inhibitors was not suggested and the effect of these agents on GAGs was not postulated.

SUMMARY OF THE INVENTION

It is an object of the present invention to provide a methods for treating a disease or condition in which up-regulating GAGs is therapeutically beneficial.

It is another object of the present invention to provide a method for treating a cartilage or skin disease or condition.

It is yet another object of the present invention to provide a method: for treating osteoarthritis.

It is yet another object of the present invention to provide a method of determining a treatment regimen in a subject in which up regulating GAGs is therapeutically beneficial.

It is yet another object of the present invention to provide a method of treating a condition or disease characterized by high levels of GAGs in a subject.

Hence, according to one aspect of the present invention there is provided a method of treating a disease or condition in which up-regulating GAGs is therapeutically beneficial comprising locally administering to a subject a therapeutically effective amount of an agent capable of down-regulating activity or expression of a component of the renin-angiotensin system, thereby treating a disease or condition in which up regulating GAGs is therapeutically beneficial.

According to further features in preferred embodiments of the invention described below, the subject exhibits low levels of GAGs.

According to still further features in preferred embodiments of the invention described below, the method further comprising analyzing GAG levels in a biological sample of the subject prior to, concomitant with and/or following administering the agent.

According to another aspect of the present invention, there is provided a method of treating a cartilage or skin disease or condition in a subject, comprising administering to a subject in need thereof a therapeutically effective amount of an agent capable of down-regulating activity or expression of a component of the renin-angiotensin system, thereby treating the cartilage or skin disease or condition in the subject.

According to further features in preferred embodiments of the invention described below, the cartilage disease is not rheumatoid arthritis.

According to yet another aspect of the present invention, there is provided a method of treating osteoarthritis in a subject, the method comprising administering to a subject in need thereof a therapeutically effective amount of an agent capable of down-regulating activity or expression of a component of the renin-angiotensin system, thereby treating osteoarthritis in the subject.

According to yet another aspect of the present invention there is provided a use of an agent capable of down-regulating activity or expression of a component of the renin-angiotensin system for the manufacture of a medicament identified for treating a cartilage or skin disease or condition.

According to yet another aspect of the present invention, there is provided a method of determining a treatment course of a disease in which up-regulating GAGs is therapeutically beneficial in a subject, the method comprising: (a) administering to a subject in need thereof a therapeutically effective amount of an agent capable of down-regulating the renin-angiotensin system; and (b) analyzing GAG level in a biological sample of said subject following (a), whereby the GAG level is indicative of the treatment course.

According to further features in preferred embodiments of the invention described below, the method further comprises obtaining an additional biological sample of the subject prior to step (a) and/or concomitant with step (b).

According to further features in preferred embodiments of the invention described below, the method further comprises comparing the GAG level in the biological sample with the additional biological sample.

According to yet another aspect of the present invention, there is provided a method of determining a treatment course in a subject suffering from a disease in which up-regulating GAGs is therapeutically beneficial, the method comprising: (a) analyzing GAG levels in a biological sample of the subject; and (b) administering to the subject a therapeutically effective amount an agent capable of down-regulating the renin-angiotensin system according to said GAG level.

According to further features in preferred embodiments of the invention described below, the method further comprises repeating step (a) following step (b).

According to still further features in the described preferred embodiments the disease or condition is selected from the group consisting of a cartilage or skin disease or condition.

According to still further features in the described preferred embodiments the agent is an angiotensin converting enzyme inhibitor.

According to still further features in the described preferred embodiments the angiotensin converting enzyme inhibitor is selected from the group consisting of AB-103, ancovenin, benazeprilat, BRL-36378, BW-A575C, CGS-13928C, CL242817, CV-5975, Equaten, EU4865, EU4867, EU-5476, foroxymithine, FPL 66564, FR-900456, Hoe-065, 15B2, indolapril, ketomethylureas, KR1-1177, KR1-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, 'RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, Asahi Brewery AB-47, alatriopril, BMS182657, Asahi Chemical C-111, Asahi Chemical C-112, Dainippon DU-1777, mixanpril, Prentyl, zofenoprilat, 1(-(I-carboxy-6-(4-piperidinyl)hexyl)amino)-1-oxop-ropyl octahydro-1H-indole-2-carboxylic acid, Bioproject BP1.137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril.

According to still further features in the described preferred embodiments agent is an NEP/ACE inhibitor.

According to still further features in the described preferred embodiments the agent is an AT1 receptor antagonist.

According to still further features in the described preferred embodiments the AT1 receptor antagonist is selected from the group consisting of Saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP-48369, DA-2079, DE-3489, DuP-167, EXP-063, EXP-6155, EXP-6803, EXP-7711, EXP-9270, FK-739, HR-720, $IC_1$-D6888, $IC_1$-D7155, $IC_1$-D8731, isoteoline, KR1-1177, L-158809, L-158978, L-159874, LR B087, LY-285434, LY-302289, LY-315995, RG-13647, RWJ-38970, RWJ-46458, S-8307, S-8308, saprisartan, saralasin, Sarmesin, WK-1360, X-6803, ZD-6888, ZD-7155, ZD-8731, BIBS39, CI-996, DMP-811, DuP-532, EXP-929, L-163017, LY-301875, XH-148, XR-510, zolasartan and PD-123319

According to still further features in the described preferred embodiments the agent is a renin inhibitor.

According to still further features in the described preferred embodiments the renin inhibitor is selected from the group consisting of enalkrein, RO 42-5892, A 65317, CP 80794, ES1005, ES 8891, SQ 34017, CGP 29287, CGP 38560, SR 43845, U-71038, A 62198, A 64662, A-69729, FK 906 and FK 744.

According to still further features in the described preferred embodiments the agent is an oligonucleotide directed to an endogenous nucleic acid sequence expressing at least one component of the renin angiotensin system.

According to still further features in the described preferred embodiments the low levels of GAGs occur in cartilage, skin or synovial fluid of the subject.

According to still further features in the described preferred embodiments the administering is effected locally.

According to still further features in the described preferred embodiments the local administering is effected by intra-articular administration, topical administration or intra-synovial administration.

According to still further features in the described preferred embodiments the intra-articular administration comprises administration into a joint selected from the group consisting of a knee, an elbow, a hip, a sternoclavicular, a temporomandibular, a carpal, a tarsal, a wrist, an ankle, an intervertebral disk and a ligamentum flavum.

According to still further features in the described preferred embodiments the cartilage disease or condition is selected from the group consisting of osteoarthritis, limited joint mobility, gout, rheumatoid arthritis, chondrolysis, scleroderma, degenerative disc disorder and systemic lupus erythematosus.

According to still further features in the described preferred embodiments the skin disease or condition is selected from the group consisting of wrinkling, psoriasis, a keloid and a burn.

According to still further features in the described preferred embodiments the local dose of said angiotensin converting enzyme inhibitor does not exceed 5 mg a day.

According to still further features in the described preferred embodiments the local dose of said AT1 receptor antagonist does not exceed 5 mg a day.

According to still further features in the described preferred embodiments the disease in which up regulating GAGs is therapeutically beneficial is selected from the group consisting of a renal disease or condition, a vascular disease or condition, a skin disease or condition and a cartilage disease or condition.

According to yet another aspect of the present invention, there is provided a method of treating a condition or disease in which down regulating GAGs is therapeutically beneficial in a subject, the method comprising administering to the subject in need thereof a therapeutically effective amount of an agent capable of up-regulating activity and/or expression of a component of a renin angiotensin system, thereby treating a condition or disease in which down regulating GAGs is therapeutically beneficial in a subject.

According to further features in the described preferred embodiments the agent is an angiotensin II agonist or angiotensin II activator.

According to still further features in the described preferred embodiments the condition is a lysosomal storage condition.

According to still further features in the described preferred embodiments the lysosomal storage condition is a mucopolysaccharidosis condition.

According to still further features in the described preferred embodiments the disease is cystic fibrosis.

According to still further features in the described preferred embodiments the administering is effected systemically.

According to still further features in the described preferred embodiments the administering is effected locally.

The present invention successfully addresses the shortcomings of the presently known configurations by providing methods and uses thereof for treating conditions or disorders associated with low or high levels of GAGs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a photograph of an electron micrograph image of a section of a control rat kidney injected with 0.9% NaCl. The photograph depicts normal podocyte architecture with numerous foot processes. FIG. 1B is a photograph of an electron micrograph image of a section of a puromycin aminonucleoside (PAN) injected rat kidney. The photograph depicts loss of podocyte architecture in the glomeruli with flattening and effacement of foot processes. In the podocyte cell body, cytoplasmatic vacuoles can be seen. FIG. 1C is a photograph of an electron micrograph image of a section of a PAN injected rat kidney together with enalapril treatment (50 mg/ml). The photograph depicts a similar loss of normal podocyte architecture.

FIG. 2A is a photograph of an electron micrograph image of a section of a control rat kidney injected with 0.9% NaCl. The photograph depicts intense CCG binding to the GBM. Original magnification ×15,000. FIG. 1B is a photograph of an electron micrograph image of a section of a PAN injected rat kidney. The photograph depicts a marked decrease in CCG binding to the GBM. In contrast, a high CCG density labeling is seen in Bowmans's capsule. Original magnification ×15,000. FIG. 2C is a photograph of an electron micrograph image of a section of a PAN injected rat kidney together with enalapril treatment (50 mg/ml). The photograph depicts intense CCG binding similar to control. Original magnification ×18,000.

FIGS. 5A-D are photographs of representative samples of histological sections of osteoarthritic(OA)-induced rats using the known OA model of partial meniscectomy of Rolli Moskowitz. FIGS. 5A-B illustrate sections of rats without any additional treatment i.e. controls (FIGS. 5A-B). FIGS. 5C-D are captopril-treated OA-induced rats (FIGS. 5C-D).

DESCRIPTION OF THE PREFERRED EMBODIMENTS

Figure 1:
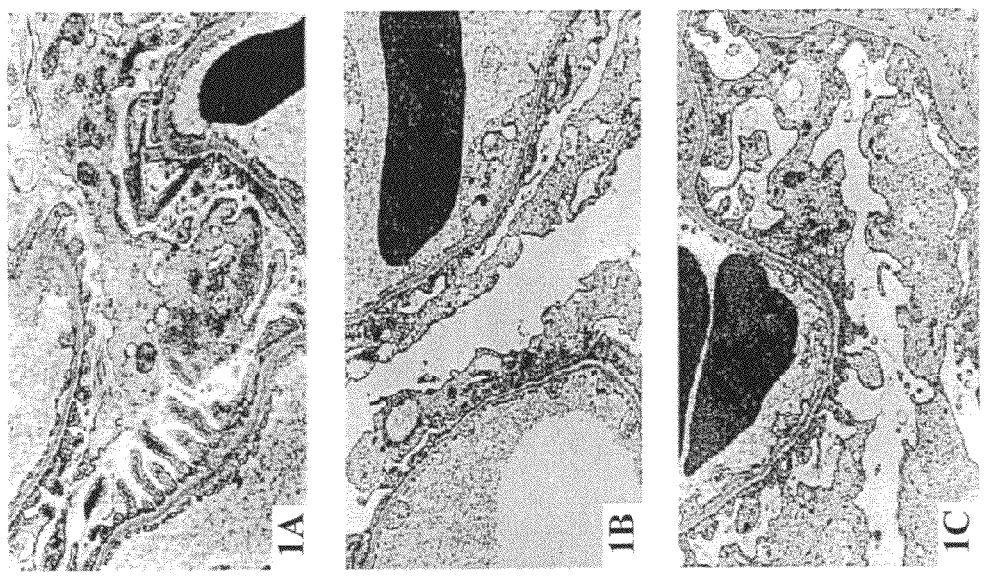
FIGS. 1A-C are photographs of electron micrograph images of thin sections of rat kidneys fixed with aldehydes and Osmium tetroxide, and embedded in araldite. Original magnification ×10,000.

The present invention relates to methods of treating diseases that would benefit from alteration in GAG levels by the administration of renin angiotensin system modulating agents.

Specifically, the present invention can be used to treat diseases that would benefit from an up-regulation of GAGs by the administration of renin angiotensin inhibitor agents and diseases that would benefit from a down-regulation of GAGs by the administration of renin angiotensin activator agents.

The principles and operation of treating conditions associated with low or high levels of GAGs may be better understood with reference to the examples and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Angiotensin II converting enzyme (ACE) inhibitors and angiotensin receptor blockers (ARBs) are generally prescribed for the management of heart failure, hypertension and myocardial infarction. They are also considered as the standard of care for preserving renal function in chronic renal disease and in renal disorders associated with proteinuria. The precise mechanism of renoprotection associated with these agents is still not defined.

One of the mechanisms involved in the pathogenesis of proteinuria in human and animal models is loss of the anionic sites in the glomerular capillary wall (GCW) [Raats C J I et al., Kidney Int 57: 385-400, 2000; Groffen A J A, et al., Nephrol Dial Transplant 14: 2119-2129, 1999]. Alterations in these sites have been demonstrated in rats with puromycin aminonucleoside (PAN) nephrosis, which has thus become a useful model for studying the pathophysiology of proteinuria.

While investigating the functional charge barrier in the glomeruli of rats with PAN nephrosis, the present inventors have unexpectedly found that the ACE-I enalapril affected glomerular anionic distribution in these rats by increasing the synthesis of GAGs (as shown in Example 1).

This is the first time the RAS pathway has been involved in the metabolism of GAGs. The present invention exploits this finding to provide a novel therapeutic modality for the treatment of diseases or conditions in which up-regulation of GAGs is therapeutically beneficial especially those that are associated with a deficiency in the levels of GAGs. The present invention also teaches novel uses of therapeutic modalities for the treatment of diseases which are associated with an increase in GAG levels.

As is illustrated herein below and in the Examples section which follows, PAN caused a significant decrease in the synthesis of chondrocyte-associated GAGs in an in-vitro system. Addition of ACE-I and angiotensin receptor blockers (ARB) led to a dose-dependent inhibition of this effect, until a complete restoration of cell-associated GAGs to control levels was achieved, as evidenced by an increased incorporation of $^{35}$S. As illustrated in Example 3 of the Examples section below, intra-articular administration of ACE-Is into an osteoarthritic rat minimized manifestations of the disease.

It will be appreciated that a number of patent applications (e.g., U.S. Pat. App. No. 20030078190 and U.S. Pat. App. No. 20030040509) have previously suggested the use of renin-angiotensin inhibitors for treating a wide range of diseases including those envisaged by the present invention. However, in sharp contrast to the present invention, both these patent applications do not suggest local administration of the renin-angiotensin modulating agent for the treatment of such conditions. The benefit of local administration is that administration of higher doses of RAS modulators may be tolerated without associated systemic side-effects.

Furthermore, the present invention provides, for the first time experimental evidence for the feasibility of treating such conditions by demonstrating that ACE-I and ARBs are able to augment chondrocyte-associated GAGs.

The therapeutic effect ACE-I quinapril was shown to suppress inflammatory arthritis in mice [Dalbeth et al., Rheumatology 44:24-31, 2004]. The ARB candesartan had a similar inhibitory effect on disease progression as well. However, local administration of the renin angiotensin system modulators was not suggested and the effect of these agents on GAGs was not postulated.

Thus, according to one aspect of the present invention there is provided a method of treating a disease or condition in which up-regulating GAGs is therapeutically beneficial.

The method of this aspect of the present invention comprising locally administering to a subject in need thereof a therapeutically effective amount of an agent capable of down-regulating activity or expression of a component of the renin-angiotensin system, thereby treating a disease or condition in which up regulating GAGs is therapeutically beneficial.

As used herein, the term "GAGs" (GlycosAminoGlycans) refers to large molecules of the extra-cellular matrix, which may also be cell-associated. GAGs are composed of repeating disaccharide units typically linked to a protein core. The disaccharide units are made of glucosamine and glucuronic acid. The position of a sulphate molecule on the N-Ac-glucosamine determines the type of GAG such as, but not limited to, hyaluronic acid, dermatan sulfate, chondroitin sulfate, heparin, heparan sulfate, and keratan sulfate or a combination thereof. GAGs of the present invention may or may not be attached to a core protein. The GAGs may be present in a tissue or part of a tissue including but not limited to cartilage, a bone, a skin, a muscle a cornea, a heart valve, an ECM of loose connective tissue, a basement membrane and a mast cell lining the arteries of lung, liver and skin tissue.

As used herein the phrase "a disease or condition in which up-regulating GAGs is therapeutically beneficial" refers to inflammatory diseases, skeletal muscle diseases, cartilage diseases and skin disorders. Examples of such diseases are further provided hereinbelow.

According to a preferred embodiment of this aspect of the present invention the treated subject preferably exhibits low levels of GAGs. Low levels of GAGs can be determined in a particular affected tissue in comparison to the same tissue area in a control healthy individual.

As used herein the phrase "low levels of GAGs" refers to low levels of normal (i.e., functional) GAGs confined to the afflicted tissue region e.g. in the cartilage, synovial fluid or skin or may be exhibited systemically. The low levels of GAGs may be as a result of a disrupted equilibrium between GAG synthesis and GAG degradation. GAG biosynthesis is regulated by the availability of the core protein as the acceptor of the sugar side chains as well as by the levels and availability of the glycosyltransferases [i.e., enzymes that catalyze the transfer of glycosyl (sugar) residues to the core protein] at the relevant intracellular sites. GAG degradation is effected primarily by the degradation of the core protein by metallopeptidases.

Low levels of GAGs may result from a decrease in core protein (proteoglycan) content as for example in osteoarthritis [Altman R D, et al., Arthritis Rheum 16:179, 1973; Jasin H E, Dingle J T, J Clin Invest 68:571-581, 1981] Alternatively, low levels of GAGs may result from upregulation of autoantibodies, such as in rheumatoid arthritis [Wang et al., P.N.A.S. 2002 Oct. 29; 99(22):14362-7]. GAG levels have also been shown to be decreased as a function of aging [Hickery et al., J. Biol. Chem., Vol. 278, Issue 52, 53063-53071], for example in the skin [Zimnitskii et al., Biomed Khim 2004, May-June; 50(3) 309-13]. GAG levels are also decreased in skin disorders associated with Lupus [Alahlafi A. M. Lupus 2004; 13(8)594-600].

As used herein the term "subject" refers to a mammal, preferably a human subject. Examples of non-human mammals include, but are not limited to mouse, rat, rabbit, bovine, horse, porcine, ovine, canine and feline.

The phrase "subject in need thereof" refers to a subject that suffers from any one of the above-diseases or is at risk of developing such a disease. Such a subject may exhibit low levels of GAGs.

As used herein the phrase "renin-angiotensin system" (RAS) refers to the cascade system that is responsible for the production of angiotensin II. In this system the protease renin cleaves the precursor angiotensinogen to produce angiotensin I which itself is cleaved to produce angiotensin II by the metallopeptidase angiotensin converting enzyme (ACE). A component of the renin angiotensin system may refer to an enzyme (e.g. renin EC 3.4.23.15 and ACE EC 3.4.15.1), subjects thereof [including angiotensinogen (K02215) and angiotensin I], receptors with which angiotensin II interacts (e.g. AT1 (NM_009585) and AT2 (NM_000686)) and downstream effectors thereof.

As used herein a "downstream effector" refers to a target molecule in a signal transduction cascade that is responsible for an effect (i.e., the increase of GAGs via the interaction of angiotensin II with its receptor). An example of a downstream effector of angiotensin II is aldosterone. Thus, components of the renin angiotensin system may also include aldosterone and aldosterone receptors.

An agent capable of down-regulating activity or expression of a component of RAS refers to a molecule such as a chemical, nucleic acid or proteinacious molecule or a combination thereof which is capable of inhibiting activity or expression of at least one component of RAS.

Agents capable of down-regulating activity or expression of proteins or mRNA transcripts encoding thereof are well known in the art.

Chemical Inhibitors

For example, an agent capable of down-regulating activity or expression of a component of RAS may be a chemical inhibitor of RAS. This includes any compound which upon administration blocks the effects of RAS on the production of GAGs by reducing the synthesis of angiotensin II or blocking its effect at the receptor.

Chemical inhibitors of the RAS include, but are not limited to, ACE inhibitors, Angiotensin II receptor antagonist, aldosterone inhibitors, aldosterone receptor antagonists, renin inhibitors and the pharmaceutically acceptable derivatives thereof including prodrugs and metabolites.

Pharmaceutically acceptable derivatives of RAS inhibitors are understood to include physiologically tolerable salts of RAS inhibitors, such physiologically tolerable salts are understood as meaning both their organic and inorganic salts, such as are described in Remington's Pharmaceutical Sciences (17th Edition, page 1418 (1985)). On account of the physical and chemical stability and the solubility, for acidic groups, inter alia, sodium, potassium, calcium and ammonium salts are preferred; for basic groups, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid are preferred.

As used herein the term "metabolite" refers to a breakdown product of the agent of the present invention following its administration e.g. hydrolysis in the liver. An example of an active metabolite is enalprilat a biotransformation product of enalapril.

The phrase "ACE inhibitor" refers to a chemical agent which is capable of at least partially down-regulating the activity of ACE (e.g., the enzymatic conversion of the physiologically inactive decapeptide form of angiotensin ("Angiotensin I") to the octapeptide form of angiotensin ("Angiotensin II"). Typical ACE inhibitors are NEP/ACE inhibitors, which are featured by neutral endopeptidase (NEP) inhibitory activity and/or angiotensin converting enzyme (ACE) inhibitory activity.

Examples of ACE inhibitors suitable for use in accordance with this aspect of the present invention include, but are not limited to AB-103, ancovenin, benazeprilat, BRL-36378, BW-A575C, CGS-13928C, CL242817, CV-5975, Equaten, EU4865, EU4867, EU-5476, foroxymithine, FPL 66564, FR-900456, Hoe-065, 15B2, indolapril, ketomethylureas, KR1-1177, KR1-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, 'RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, Asahi Brewery AB-47, alatriopril, BMS182657, Asahi Chemical C-111, Asahi Chemical C-112, Dainippon DU-1777, mixanpril, Prentyl, zofenoprilat, 1(-(I-carboxy-6-(4-piperidinyl) hexyl)amino)-1-oxop-propyl octahydro-1H-indole-2-carboxylic acid, Bioproject BP1.137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril.

Such ACE inhibitors are commercially available. For example, the ACE inhibitor ramipril (known from EP 79022) is sold by Aventis, e.g. under the trademark Delix® or Altace®. Enalapril or Enalapril Maleate, and Lisinopril are two sold by Merck and Co and Sigma (cat no. 0773). Enalapril is sold under the trademark Vasotec®. Lisinopril is sold under the trademark Prinivil®.

Examples of NEP/ACE inhibitors suitable for use herein include those disclosed in U.S. Pat. Nos. 5,508,272, 5,362,727, 5,366,973, 5,225,401, 4,722,810, 5,223,516, 5,552,397, 4,749,688, 5,504,080, 5,612,359, 5,525,723, 5,430,145, and 5,679,671, and European Patent Application Nos. 0481522, 0534263, 0534396, 0534492 and 0671172.

The phrase "angiotensin II receptor antagonist" refers to a chemical agent which is capable of partially or completely down-regulating an activity of angiotensin II (e.g., decreasing GAGs) by binding to an angiotensin receptor, preferably to the AT1 receptor.

Examples of angiotensin II receptor antagonists suitable for use in accordance with this aspect of the present invention include, but are not limited to Saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI-D6888, ICI-D7155, ICI-D8731, isoteoline, KR1-1177, L-158809, L-158978, L-159874, LR B087, LY-285434, LY-302289, LY-315995, RG-13647, RWJ-38970, RWJ-46458, S-8307, S-8308, saprisartan, saralasin, Sarmesin, WK-1360, X-6803, ZD-6888, ZD-7155, ZD-8731, BIBS39, CI-996, DMP-811, DuP-532, EXP-929, L-163017, LY-301875, XH-148, XR-510, zolasartan and PD-123319. Theseinhibitors are commercially available.

Examples of renin inhibitors suitable for use in accordance with this aspect of the present invention include, but are not limited to enalkrein; RO 42-5892; A 65317; CP 80794; ES1005; ES 8891; SQ 34017; CGP 29287; CGP 38560; SR 43845; U-71038; A 62198; A 64662, A-69729, FK 906 and FK 744.

The phrase "aldosterone inhibitor" refers to a chemical agent which is capable of partially or completely down-regulating an activity of aldosterone (i.e., decreasing GAGs) via a pre-receptor mechanism by directly or indirectly reducing or preventing the synthesis or activity of aldosterone.

Examples of aldosterone inhibitors of the present invention include, but are not limited to, Aromatase inhibitors such as R-76713, R-83842, CGS-16949A (fadrozole), CGS-20267 (letrozole), CGS-20267, aminoglutethamide, CGS-47645, ICI-D-1033, chromone & xanthone derivatives, and YM-511; 12-Lipoxygenase inhibitors such as PDGF, TNF, IL-1, IL-1 beta, BW755c, phenidone, baicalein, aminoguanidine, nordihydroguaiaretic acid (NDGA), cinnamyl-3,4-dihydroxy-alpha-cyanocinna-mate (CDC), panaxynol, pioglitazone, and mRNA cleaving ribozyme; $P450.sub.11.beta.$ inhibitors such as 18-vinylprogesterone, and 18-ethynylprogesterone, fatty acids such as oleic acid; 18-vinyldeoxycorticosterone, ketoconazole, clotrimazole, miconazole, etomidate, spironolactone, and 23-0586; Atrial natriuretic factors such as ANP, ANF and ANF fragments; 17, 20 Lysase inhibitors such as YM-55208, and YM-53789; Prostaglandin synthesis inhibitors such as indomethacin, meclofenamate, aminoglutethamide, and aspirin; PKC inhibitors such as sphingosine, retinal, H-7, staurosporine, and trifluoperazine; Benzodiazepines such as diazepam and midazolam; Calcium blockers such as amlodipine, and mibefradil; Diacylglycerol lipase inhibitors such as RHC-80267 [1,6-bis-(cyclohexyloximinocarbonylamino)-hexane]; Potassium ionophores such as valinomycin, and cromakalim; Electron transport blockers (metabolic inhibitors) such as antimycin A, cyanide, rotenone, and amytal; Dopamine (prolactin inhibiting hormone), Chlorbutol, 18-ethynyl-1'-deoxycorticosterone (18-EtDOC); and ethanol.

The phrase "aldosterone antagonist" refers to a chemical agent which is capable of partially or completely down-regulating an activity of aldosterone (i.e., decreasing GAGs) by binding to an aldosterone receptor.

Examples of aldosterone antagonists include but are not limited to spironolactone, aldactone, drospirenone, epoxymexrenone and eplerenone.

Protein Agents

Another example of an agent capable of down-regulating RAS is an antibody or antibody fragment capable of specifically binding and at least partially down-regulating activity (i.e., neutralizing antibody) of a component of RAS. For example, the antibody may bind to ACE, preferably to one of its two catalytic domains, thereby preventing its function. Alternatively, the antibody or antibody fragment may bind to an activation site present in ACE. ACE secretase is responsible for cleaving the membrane bound form of ACE so it may be released into extracellular fluids (such as plasma, and seminal and cerebrospinal fluids) as a soluble enzyme in a process known as 'shedding'. Antibodies raised against the shedding domain of ACE that prevent the shedding process are known in the art e.g. mAb 3G8 [Balyasnikova et al., Biochem. J. (2002) 362 (585-595)]. Other monoclonal antibodies raised against ACE are commercially available (e.g. Cat. # ACE23-MADI, San Antonio, U.S.A.).

Antibodies are also commercially available for renin (e.g. Catalog No: RDI-rtreninabm) and Angiotensinogen (e.g. Catalog No: RDI-rtangtenabm), both from Research Diagnostics, New Jersey, U.S.A.

Preferably, the antibody specifically binds to at least one epitope of the protein. As used herein, the term "epitope" refers to any antigenic determinant on an antigen to which the paratope of an antibody binds. Epitopes of ACE catalytic domain preferably include Arg-1203 and Ser-1204 [Parkin et al., Protein and Peptide Letters, October 2004, vol. 11, no. 5, pp. 423-432(10)].

Epitopic determinants usually consist of chemically active surface groups of molecules such as amino acids or carbohydrate side chains and usually have specific three-dimensional structural characteristics, as well as specific charge characteristics.

The term "antibody" as used in this invention includes intact molecules as well as functional fragments thereof, such as Fab, F(ab')2, and Fv that are capable of binding to the antigen presented by the macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bridges; (4) Fv, defined as a genetically engineered fragment containing the variable region of the light chain and the variable region of the heavy chain expressed as two chains; and (5) Single Chain Antibody ("SCA"), a genetically engineered molecule containing the variable region of the light chain and the variable region of the heavy chain, linked by a suitable peptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., [Proc. Natl. Acad. Sci. USA 69:2659-62 (1972)]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single peptide chain with a linker peptide bridging the two V domains. Methods for producing sFvs are described, for example, by [Whitlow and Filpula [(1991), Methods 2: 97-105]; Bird et al., [(1988) Science 242:423-426]; Pack et al., [(1993), BioTechnology 11:1271-77]; and U.S. Pat. No. 4,946,778, which is hereby incorporated by reference.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [(1991) Human Antibodies and Hybridomas, 2:172-189 and U.S. Pat. No. 6,580,016].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source that is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1992); Marks et al., J. Mol. Biol., 222:581 (1991)]. The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,806; 5,545,807; 5,569,825; 5,625,126; 5,633,425; 5,661,016, and in the following scientific publications: Marks et al., BioTechnology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Alternatively, another proteinaceous agent capable of down-regulating the activity of a RAS can be a non-functional derivative thereof (i.e. dominant negative). ACE forms, which include mutations that render the protein inactive, are known in the art [Rigat et al., J Clin Invest 86, 1343]. Mutations may also occur in the renin gene. These include, for example, two nonsense mutations [Hasimu et al., Hypertension. 2003 February;41(2):308-12; Villard et al., J Biol. Chem. 1994 Dec. 2;269(48):30307-12.]

Peptides which mimic these non-functional derivatives and others can be synthesized using solid phase peptide synthesis procedures that are well known in the art and further described by John Morrow Stewart and Janis Dillaha Young, [Solid Phase Peptide Syntheses (2nd Ed., Pierce Chemical Company, 1984)]. Synthetic peptides can be purified by preparative high performance liquid chromatography [Creighton T. (1983) Proteins, structures and molecular principles. WH Freeman and Co. N.Y.] and the composition of which can be confirmed by amino acid sequencing.

In cases where large amounts of the peptide are desired, they can be generated using recombinant techniques such as described by Bitter et al., (1987) Methods in Enzymol. 153: 516-544, Studier et al., (1990) Methods in Enzymol. 185:60-89, Brisson et al., (1984) Nature 310:511-514, Takamatsu et al., (1987) EMBO J. 6:307-311, Coruzzi et al., (1984) EMBO J. 3:1671-1680 and Brogli et al., (1984) Science 224:838-843, Gurley et al., (1986) Mol. Cell. Biol. 6:559-565 and Weissbach & Weissbach, 1988, Methods for Plant Molecular Biology, Academic Press, N.Y., Section VIII, pp 421-463.

Nucleic Acid Agents

Alternatively, the agent of this aspect of the present invention may be an oligonucleotide directed against an endogenous nucleic acid sequence expressing the component participating in the RAS.

A small interfering RNA (siRNA) molecule is an example of an oligonucleotide agent capable of downregulating a component participating in RAS. RNA interference is a two-step process. During the first step, which is termed the initiation step, input dsRNA is digested into 21-23 nucleotides (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner. Successive cleavage events degrade the RNA to 19-21 bp duplexes (siRNA), each strand with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al., (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC [Hammond et al., Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be affected as follows. First, the mRNA sequence target is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and significantly reduced protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

An example where dsRNA was used to successfully inhibit an ACE is provided by Brooks et al., [J. Biol. Chem., Vol. 278, Issue 52, 52340-52346, 2003].

Another oligonucleotide agent capable of down-regulating a component participating in RAS is a DNAzyme molecule capable of specifically cleaving an mRNA transcript or a DNA sequence of the target. DNAzymes are single-stranded polynucleotides which are capable of cleaving both single and double stranded target sequences (Breaker, R. R. and Joyce, G. Chemistry and Biology 1995;2:655; Santoro, S. W. & Joyce, G. F. Proc. Natl, Acad. Sci. USA 1997;94:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of Chronic Myelogenous Leukemia (CML) and Acute Lymphocytic Leukemia (ALL).

Down-regulation of a component participating in RAS can also be effected by using an antisense polynucleotide capable of specifically hybridizing with an mRNA transcript encoding the component participating in the RAS (e.g., an antisense oligonucleotide directed at one of the two catalytic sites of ACE).

Design of antisense molecules, which can be used to efficiently down-regulate a component participating in the RAS system, must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a way that inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al., Blood 91: 852-62 (1998); Rajur et al., Bioconjug Chem 8: 935-40 (1997); Lavigne et al., Biochem Biophys Res Commun 237: 566-71 (1997) and Aoki et al., (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al., Biotechnol Bioeng 65: 1-9 (1999)].

Such algorithms have been successfully used to implement an antisense approach in cells. For example, the algorithm developed by Walton et al., enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved to be effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Homlund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Antisense-mediated suppression of genes in the RAS has also been successfully performed e.g. inhibition of angiotensinogen synthesis [Schinke et al., Hypertension. 1996, 27:508-513]

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for down-regulating expression of known sequences without having to resort to undue trial and error experimentation.

Another agent capable of down-regulating a component of RAS is a ribozyme molecule capable of specifically cleaving an mRNA transcript encoding a component participating in RAS. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—www.rpi.com/index.html).

An additional method of regulating the expression of a component of RAS genes in cells is via triplex forming oligonucleotides (TFOs). In the last decade, studies have shown that TFOs can be designed which can recognize and bind to polypurine/polypirimidine regions in double-stranded helical DNA in a sequence-specific manner. These recognition rules are outlined by Maher III, L. J., et al., Science (1989) 245: 725-730; Moser, H. E., et al., Science (1987)238:645-630; Beal, P. A., et al., Science (1991) 251:1360-1363; Cooney, M., et al., Science (1988)241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer (2003) J Clin Invest; 112:487-94).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch (2002), BMC Biochem, September 12, Epub). The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. (1999) 27:1176-81, and Puri, et al., J Biol Chem, (2001) 276:28991-98), and the sequence- and target-specific downregulation of expression of the Ets2 transcription factor, important in prostate cancer etiology (Carbone, et al., Nucl Acid Res. (2003) 31:833-43), and the pro-inflammatory ICAM-1 gene (Besch et al., J Biol Chem, (2002) 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res (2000); 28:2369-74).

Additionally, TFOs designed according to the abovementioned principles can induce directed mutagenesis capable of effecting DNA repair, thus providing both downregulation and upregulation of expression of endogenous genes [Seidman and Glazer, J Clin Invest (2003) 112:487-94]. Detailed description of the design, synthesis and administration of effective TFOs can be found in U.S. Patent Application Nos. 2003 017068 and 2003 0096980 to Froehler et al., and 2002 0128218 and 2002 0123476 to Emanuele et al., and U.S. Pat. No. 5,721,138 to Lawn.

Additional description of oligonucleotide agents is further provided hereinbelow. It will be appreciated that therapeutic oligonucleotides may further include base and/or backbone modifications, which may increase bioavailability, therapeutic efficacy and reduce cytotoxicity. Such modifications are described in Younes (2002) Current Pharmaceutical Design 8:1451-1466.

For example, the oligonucleotides of the present invention may comprise heterocylic nucleosides consisting of purines and the pyrimidines bases, bonded in a 3' to 5' phosphodiester linkage.

Preferably used oligonucleotides are those modified in backbone, internucleoside linkages or bases, as is broadly described herein below.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidates and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e. the backbone, of the nucleotide units are replaced with novel groups. The base units are maintained for complementation with the appropriate polynucleotide target. An example for such an oligonucleotide mimetic includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al., (1993) Antisense Research and Applications, CRC Press, Boca Raton 276-278] and are presently preferred base substitutions, even more particularly when combined with 2'-O-methoxyethyl sugar modifications.

Examples of oligonucleotide agents which have been used to down-regulate expression of RAS proteins are described in (Morishita et al., Arteriosclerosis, Thrombosis, and Vascular Biology 2000; 20:915).

Recombinant agents or oligonucleotide agents of the present invention can be administered to the subject employing any suitable mode of administration, described hereinbelow (i.e. in vivo gene therapy). Alternatively, the nucleic acid construct can be introduced into a suitable cell using an appropriate gene delivery vehicle/method (transfection, transduction, etc.) and an appropriate expression system. The modified cells are subsequently expanded in culture and returned to the individual (i.e. ex vivo gene therapy). Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and transcription of the transgene is directed from the CMV promoter. Vectors derived from Mo-MuLV are also included such as pBabe, where the transgene will be transcribed from the 5'LTR promoter.

It will be appreciated that nucleic acid agents of the present invention can be can be introduced to the subject using the well known "gene knock-in strategy" which will result in the formation of a non-functional protein [see e.g., Matsuda et al., Methods Mol. Biol. 2004; 259:379-90], such as by mimicking natural mutations of the RAS system.

The amino acid sequence of ACE together with its 3-D structure makes it a relatively easy target for point mutations and gene knock-in strategy. The enzyme is made up of two catalytic domains each of which comprises a chloride binding centre which are absolutely required for the activation of the enzyme. Thus a point mutation in either of these sites would render the ACE inactive and could be introduced to the subject using the gene knock-in approach as mentioned herein. An example of a naturally occurring ACE point mutation known in the art includes the point mutation causing Pro1199Leu in the stalk region [Kramers et al., Circulation. 2001; 104: 1236].

As mentioned agents of the present invention may be used for treating any disorder which would benefit from an up-regulation of GAGs.

As used herein in the specification and claims section that follows the terms "treatment" and "treating" refers to preventing, curing, reversing, attenuating, alleviating, minimizing, suppressing or halting the deleterious effects of the disease.

An example of a group of diseases or conditions in which increasing GAG levels may be therapeutically beneficial include inflammatory disorders [Chou et al., Exp Biol Med 2005, April, 230(4) 255-62]. As used herein the phrase "inflammatory disorders" includes but is not limited to chronic inflammatory diseases and acute inflammatory diseases. Examples of such diseases and conditions are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July;15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med. Sci. 2000 April; 319 (4):234), myasthenic diseases, Lambert-Eaton myasthenic syndrome (Takamori M. Am J Med. Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala 0. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel LH. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11(6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May;

57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3): 139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2): 157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Komberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E.

et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2: S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

As mentioned hereinabove, the inflammatory disorder rheumatoid arthritis may benefit from an increase in GAGs. This has been shown by Dalbeth et al [Rheumatology 44:24-31, 2004]. Other arthritic disorders which may benefit from an elevation in GAG levels includes osteoarthritis [Richy F, Arch Intern Med 163:1514-1522, 2003].

As used herein, the term "osteoarthritis" refers to the arthritic disorder involving progressive deterioration of articular cartilage with minimal inflammation [Schoenherr et al. in Small Animal Clinical Nutrition 4.sup.th Ed., Hand et al. Eds., Walsworth Publishing Company, Marceline, Mo., 2000, 907-921; Hedbom et al., Cell Mol. Life. Sci 59:45-53, 2002; Pool, Front Biosci 4:D662-70, 1999].

Another example of a group of diseases or conditions in which increasing GAG levels may be therapeutically beneficial includes those that effect skeletal muscle. GAG mimetics were shown to promote skeletal muscle repair [Zimowska M. J. Cell Physiol, 2005 May 10]. Examples of skeletal muscle disorders which may benefit from an increase in GAGs include the muscular dystrophies, the structural myopathies, the inflammatory myopathies, myotonic disorders, channelopathies, and metabolic muscle diseases.

Urinary bladder infections and tumors are also associated with a decrease in GAGs and provide a further example of a condition which would benefit from their administration [Kyker K. D. et al., BMC Urol. 2005 Mar. 23; 5(1):4; Cengiz N. et al., Pediatr Nephrol. 2005 May 5].

Other examples of specific diseases which may benefit from the administration of GAGs are cervical cancer [Shinyo et al., Gynecol Oncol 2005, March 96(3) 776-83]; Alzheimers disease [Ubranyi Z et al., Neurochem Int. 2005 May 46(6) 471-7]; degenerative disc disorder [Stoeckelhuber M, Ann Anat. 2005 March; 187(1):35-42] and diabetic neuropathy [Lensen et al., J. Am. Soc. Nephrol. 2005 May 16(5) 1279-88].

Ocular complications have also been shown to benefit from an elevation in GAG levels, e.g. the sealing of corneal incisions [Reyes et al., Inves Opthalmol V is Sci 2005, April 46(4) 1247-50] and ocular complications associated with MPS [Ashworth J. L. Eye 2005, May 20].

Since GAGs are such an important component of cartilage and are essential for the functioning of this tissue in normal joint movement, one preferred group of disorders are cartilage disorders. As described in the Examples section hereinbelow, the ACE-I Enalaprilat and the ARB Candesartan both significantly increased GAG synthesis to control levels as evidenced by an increased incorporation of $^{35}$S.

As used herein, "a cartilage disorder" refers to any disorder which affects the functioning or causes pain in a tissue which comprises cartilage such as a joint. As used herein the term "a joint" refers to e.g. a knee, elbow, hip, stemoclavicular, temporomandibular, carpal, tarsal, wrist, ankle, intervertebral disk or ligamentum flavum.

Examples of cartilage disorders include but are not limited to osteoarthritis limited joint mobility, gout, rheumatoid arthritis, chondrolysis, fibromyalgia scleroderma, tendonitis, spondylitis, degenerative disc disorder, systemic lupus erythematosus and carpal tunnel syndrome.

GAGs also play a vital role in skin and thus belong to another preferred group of disorders. GAGs have been shown to benefit skin conditions associated with skin aging e.g. wrinkling [Isnard et al., Biomed Pharmacother. 2004 April; 58(3):202-4; Titz et al., Am J Physiol Heart Circ Physiol. 2004 September; 287(3):H1433; Nomura et al., J. Dermatol.

2003 September; 30(9):655-64], psoriasis [Verges, Med Clin (Barc). 2004 Nov. 27; 123(19):739-42], a keloid [Alaish et al., J Pediatr Surg. 1995 July; 30(7):949-52] and burn [Heitland et al., Burns. 2004 August; 30(5):471-5].

The present invention also envisages treating a disease or condition in which down regulating GAGs is therapeutically beneficial in a subject, the method comprising administering to the subject in need thereof a therapeutically effective amount of an agent capable of up-regulating activity and/or expression of a component of a renin angiotensin system, thereby treating a condition or disease in which down regulating GAGs is therapeutically beneficial in a subject.

Examples of conditions in which down regulating GAGs may be of therapeutic benefit are those that are characterized by high levels of GAGs including lysosomal storage diseases such as mucopolysaccharidoses (MPS), including but not limited to Hurler's syndrome, Hunter's syndrome, Sanfilippo syndrome, Maroteaux-Lamy syndrome and Morquio's syndrome.

Another example of a disease in which down regulating GAGs may be therapeutically beneficial is cystic fibrosis [Khatri et al., Pediatr Res. 2003 April; 53(4):619-27].

Agents capable of up-regulating activity of a component of a renin angiotensin system (RAS) include the members themselves of RAS including the enzymes ACE (EC 3.4.15.1) or renin (EC 3.4.23.15). Other agents capable of up-regulating a component of RAS are chemical agents or peptide agents acting as agonists at the AT receptors (e.g. L-162,313) or activators of ACE [Elisseeva et al., Biochem Mol Biol Int. 1993 July; 30(4):665-73] or renin.

Agents capable of up-regulating expression of a component of RAS may also include exogenous polynucleotide sequence designed and constructed to express at least a functional portion of a member of RAS. Accordingly, the exogenous polynucleotide sequence may be a DNA or RNA sequence encoding a member of RAS, capable of decreasing the level of GAGs. The phrase "functional portion" as used herein refers to a part of the renin or ACE (i.e., a polypeptide) which is sufficient to exert an activity (i.e., reduction of GAGs). Gene therapy techniques for the administration of these genes are discussed herein above.

The RAS modulating agents (i.e., for up-regulating or down-regulating GAGs, as described above) of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the RAS modulating agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Agents of the present invention are preferably administered locally for example, via injection of the pharmaceutical composition directly into a tissue region of a patient.

Local methods of administration for particular disorders are detailed hereinbelow in Table 1:

TABLE 1

| Disorder or Condition | Local method of adminitration |
| --- | --- |
| Cartilage disorders | Intra-articular/Intra-synovial |
| Skin disorders | Topical |
| Muscular disorders | Intra-muscular |
| Degenerative disc disorders | Direct injection into the disc area |
| End stage renal disease treated by peritoneal dialysis | Directly into the peritoneal cavity via dialysis fluid |
| Alzheimers | Directly into the brain |
| Urinary bladder infection | Via a catheter to the bladder |
| Ocular disorders | Topical |

For topical application, the RAS modulators of the present invention may be suspended in a gel suitable for topical applications. Other examples of pharmaceutical compositions suitable for topical, transmucosal or transnasal applications include, but are not limited to creams, ointments, pastes, lotions, milks, suspensions, foams and serum.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The pharmaceutical composition of the present invention may also be formulated as an extended or a sustained-release composition especially for the treatment of arthritic disorders described herein above.

The phrase "extended-release" or "sustained-release" formulation refers to a formulation of an agent of the present invention resulting in the release or activation of the active inhibitor for a sustained or extended period of time—or at least for a period of time which is longer than if the agent-was made available in vivo in the native or unformulated state. Optionally, the extended-release formulation occurs at a constant rate and/or results in sustained and/or continuous concentration of the active polypeptide. Suitable extended release formulations may comprise microencapsulation, semi-permeable matrices of solid hydrophobic polymers, biogradable polymers, biodegradable hydrogels, suspensions or emulsions (e.g., oil-in-water or water-in-oil). Optionally, the extended-release formulation comprises poly-lactic-co-glycolic acid (PLGA) and can be prepared as described in Lewis, "Controlled Release of Bioactive Agents form Lactide/Glycolide polymer," in Biodegradable Polymers as Drug Delivery Systems, M. Chasin & R. Langeer, Ed. (Marcel Dekker, New York), pp. 1-41. Optionally, the extended-release formulation is stable and the activity of the RAS inhibitor does not appreciably diminish with storage over time. More specifically, such stability can be enhanced through the presence of a stabilizing agent such as a water-soluble polyvalent metal salt.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose e.g. inhibition of ACE or blockage of angiotensin II receptor. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

One method of determining a therapeutically effective amount of the RAS inhibitor of the present invention is by analyzing GAG levels prior to, concomitant with and/or following administering of the agent. In doing so, additional information may be gleaned pertaining to the determination of treatment regimen, treatment course and/or to the measurement of the severity of the disease.

GAG levels may be measured by removing a biological fluid (e.g. synovial fluid) or tissue (e.g. cartilage) from the subject using techniques known in the art. Methods of measuring GAGs are known in the art and include those described below in Examples 1 and 2. Preferably, GAG levels in the analyzed sample are compared with GAG levels from a control individual. It is preferable that the control sample come from a subject of the same species, age and from the same sub-tissue. Alternatively, control data may be taken from databases and literature.

Conceivably the analyzing GAG levels and administering steps may be repeated a number of times during the course of a treatment. For instance the GAG levels may be analyzed one week following administration of the agent. If the GAG levels are higher than those compared with a control, the dose of the agent may be decreased. If the GAG levels remain lower than those compared with a control, the dose of the agent may be increased.

In preferred embodiments of this aspect of the present treatment courses may be determined in this way for any disease in which up regulating GAGs is therapeutically beneficial including but not limited to renal diseases or conditions, vascular diseases or conditions, skin diseases or conditions and cartilage diseases or conditions. These diseases may be associated with a decrease in GAGs as illustrated in the Examples section below. Specifically, as seen from the in vivo results in Example 1, FIGS. 2A-C and 3A-C and the in vitro results in Example 2, FIG. 4 and Table 3, GAGs are reduced in renal diseases associated with proteinuria. Example 2, table 4 illustrates the decrease of GAGs in endothelial cells and Example 2, table 5 illustrates the decrease in GAGs in chondrocytes.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually so that local levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Locally administered therapeutic doses of agents of the present invention (e.g., angiotensin converting enzyme inhibitor, AT1 receptor antagonist) preferably do not exceed about 10 mg, preferably do not exceed about 9 mg, preferably do not exceed about 8 mg, preferably do not exceed about 7 mg, preferably do not exceed about 6 mg, preferably do not exceed about 5 mg, preferably do not exceed about 4 mg, preferably do not exceed about 3 mg, preferably do not exceed about 2 mg, preferably do not exceed about 1 mg, preferably do not exceed about 0.5 mg, preferably do not exceed about 0.1 mg.

Systemic doses for systemic administration of the agents of the present invention can be determined according to the subject's need, such as for example 1-250 mg of agent/day.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The agents of the present invention may also be administered in combination with other pharmaceutical agents. An example of a combination therapy may be for the treatment of lysosomal storage diseases. As mentioned herein above lysosomal storage diseases such as MPS are associated with mutations in lysosomal hydrolase enzymes. Thus, preferably the lysosomal hydrolase enzyme is also administered to the patient together with the RAS activating agent. One method of introducing an enzyme to a patient is by using gene therapy techniques as discussed herein above.

Another example, is illustrated in renal patients. A common problem associated with patients suffering from end stage renal disease treated by peritoneal dialysis is the reduction of anionic sites that are critical to its selective permeability, thereby impairing the peritoneal transport properties in patients on long-term peritoneal dialysis (PD). It is believed that the high concentration of glucose in the dialysis fluid required for the fluids' high osmolality is responsible for the membrane's loss of function and it has been shown that glucose affects the membrane by reducing its GAG content [Yung et al., J Am Soc Nephrol. 2004 May; 15(5):1178-88]. Thus, agents of the present invention may be added to the dialysis fluid in order to increase GAG levels in the peritoneal mesothelium thereby ameliorating the deleterious effects of high glucose concentrations.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

Example 1

Investigation of the Functional Charge Barrier in the Glomeruli of Rats with PAN Nephrosis The objective of this study was to ascertain in vivo whether inhibition of RAS by administration of ACE-I increased GAG synthesis following puromycin administration using electron microscopy morphology and histochemistry techniques.

Materials and Methods

Animals and treatment regimen—Twenty-six male Wistar rats (Belinson, Israel, 220-260 gr each) were housed in individual metabolic cages, and allowed free access to a standard diet and water. Following an acclimatization period of 3 days, the rats were randomized into three groups: controls, puromycin aminonucleoside-treated (PAN-treated) and PAN+ enalapril treated. Six controls were injected with 0.9% NaCl, and 20 rats were injected with PAN (75 mg/kg, Sigma, St. Louis, Mo.) through the tail vein. Ten of the latter were treated with enalapril (Merck Research Laboratories, 50 mg/L) in their drinking water 3 days prior to PAN injection. On day 9, 24-hour urine collections were performed and the protein content was measured using the Beckman Array-Protein system. On day 10, rats were weighed and blood was collected for measurement of serum albumin, creatinine and cholesterol (Autoanalyzer, Hitachi, Japan). All animal experimentation was conducted according to the guidelines established by the Rabin Medical Center ethical committee for the Care and Use of Laboratory Animals Tissue preparation: The kidneys were removed rapidly and placed on ice and the cortices were separated from the medulla. Slices of each kidney were fixed in 0.5% glutaraldehyde in phosphate buffered saline (PBS), pH 7.4 for morphological and histochemical studies. For electron microscopy (EM), 1 mm$^3$ tissue blocks of GA-fixed kidneys were washed, dehydrated in ethanol, and embedded in LR-white resin (Polysciences, Wash. Pa.). For EM morphology, similar tissue blocks were post-fixed with 1% Osmium tetroxide ($OsO_4$) in Veronal-acetate buffer, pH 7.4, for 1 hour at 4° C., dehydrated in ethanol and propylene oxide, and embedded in araldite (Polysciences).

Electron microscopy morphology and histochemistry: For EM morphology, ultrathin araldite sections were mounted on 400 mesh grids, stained with uranyl acetate and lead citrate, and coated with carbon. F or EM histochemistry, ultrathin LR-white sections were mounted on 200 mesh nickel grids, coated with formvar films and impregnated with carbon. Polycationic colloidal gold (CCG) was prepared by stabilization of colloidal gold, 12 nm with poly-L-lysine, as described by Weinstein et al., [J Am Soc Nephrol 8: 586-595, 1997]. The sections were stained with CCG, rinsed, and stained with saturated uranyl acetate in 50% ethanol. Examination of all sections was carried out using a JEOL-100B EM at 80 KV.

Morphometry: Analysis of the CCG labeling densities was performed in a blind manner on LR-white-embedded kidney tissue stained with CCG. Analysis was carried out by calculating the density of gold particles/1 $\mu m^2$ area of randomly cut membranes. Five rats from each group were studied. In each rat, 100 measurements from 10 glomeruli were performed. All measurements were carried out on digitized electron micrographs at a magnification of 5000, using the NIH-Image 1.49 program for the Macintosh.

Results

The results of the blood and urine tests are shown in Table 2, below.

TABLE 2

| | Control | PAN | PAN + enalapril |
|---|---|---|---|
| serum creatinine mg/dl | 0.60 ± 0.01 | 0.60 ± 0.01 | 0.60 ± 0.02 |
| serum albumin g/dl | 2.9 ± 0.0 | 2.1 ± 0.1* | 2.3 ± 0.1** |
| serum cholesterol mg/dl | 82.8 ± 5.5 | 132.4 ± 14.3* | 91.7 ± 10.7 |
| proteinuria mg/24 h | 12.3 ± 4.9 | 97.2 ± 15.6* | 47.1 ± 12.4*** |

PAN-puromycin aminonucleoside.
*$p < 0.001$ vs control,
**$p < 0.005$ vs control,
***$p < 0.02$ vs control and vs PAN.

Serum albumin was lower in the PAN groups compared to control, both in non-treated ($p<0.001$), and in enalapril-treated ($p<0.005$) rats. Serum cholesterol was significantly higher in the PAN group ($p<0.001$). Twenty-four hour urine collections showed significant proteinuria in the non-treated PAN group ($p<0.001$), which improved in the enalapril-treated PAN group ($p<0.02$).

Morphology: Electron microscopy analysis of the control rats showed normal podocyte architecture with numerous foot processes (FIG. 1A). However, in PAN rats the glomeruli exhibited loss of podocyte architecture with flattening and effacement of foot processes (FIG. 1B). In the podocyte cell body cytoplasmatic vacuoles could be seen. No changes were observed in the glomerular basement membrane (GBM) or in the endothelium. In the enalapril-treated PAN rats there was also a similar loss of normal podocyte architecture (FIG. 1C).

Figure 2:
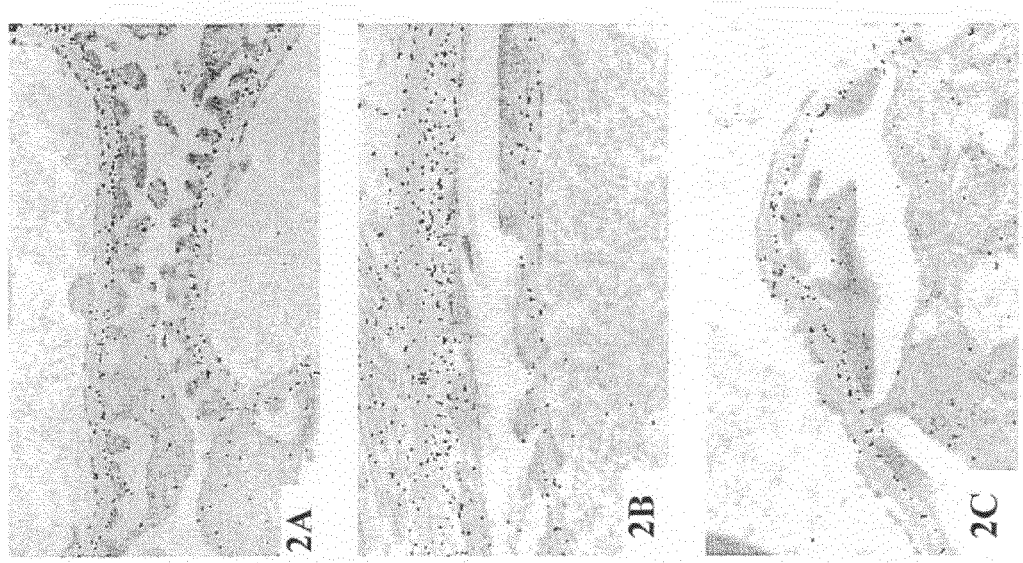
FIGS. 2A-C are photographs of electron micrograph images of sections of rat kidneys fixed with aldehydes embedded in LR-white and labeled with CCG.
Figure 3:
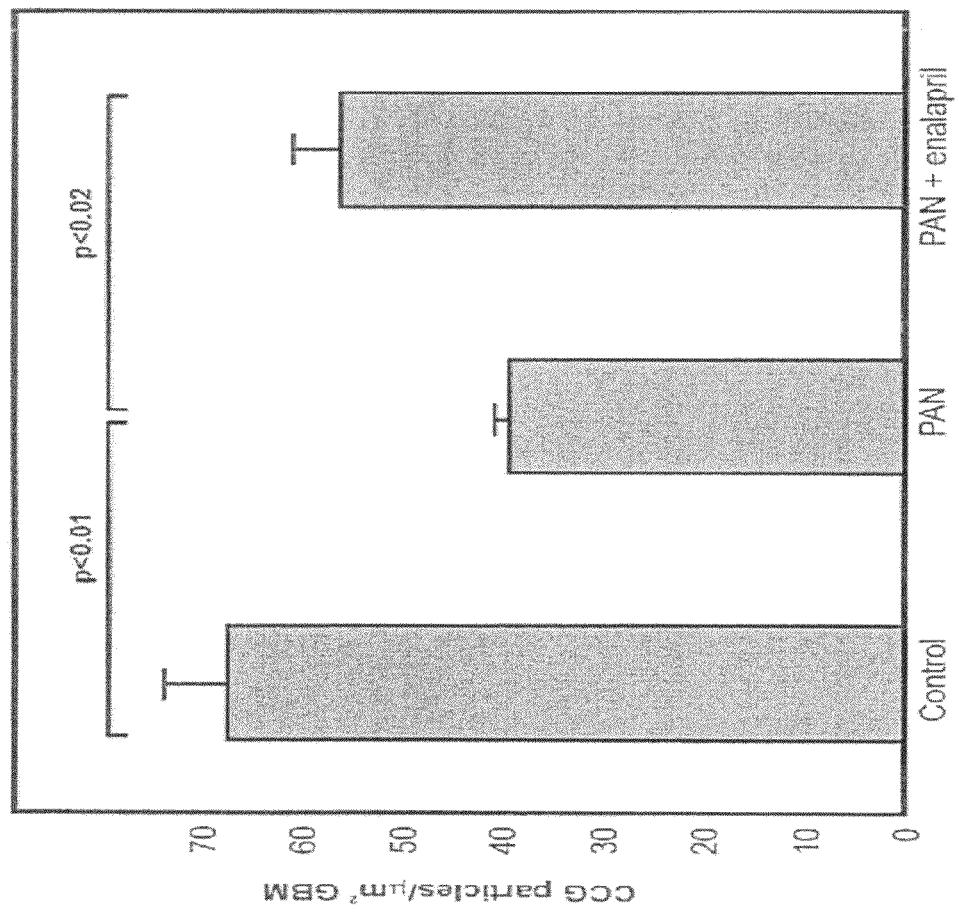
FIG. 3 is a bar graph illustrating the morphometric analysis of CCG binding to the GBM on thin LR-white kidney sections. The results are depicted as the number of CCG particles bound to $\mu m^2$ GBM comparing CCG density in control kidneys, PAN kidneys and enalapril-treated PAN kidneys.

Binding of CCG to the GBM: Morphometric analysis of CCG staining by electron microscopy showed that binding of CCG was mainly restricted to the GBM, Bowman's capsule, and basement membranes of tubuli and blood vessels. Glomerular CCG binding is illustrated in FIGS. 2A-C. The results of the morphometric analysis are illustrated in FIGS. 3A-C. In the control group there were 67.3+5.6 particles/$\mu m^2$ GBM (FIG. 3A); in the non-treated PAN group CCG binding was significantly reduced to 39.1±1.0 particles/$\mu m^2$ GBM ($p<0.001$ vs control, FIG. 3B), and in the enalapril-treated PAN group, CCG binding increased to 56.0±5.5 particles/$\mu m^2$ GBM ($p<0.02$ vs PAN, NS vs control, FIG. 3C). These results demonstrate that in nephrotic PAN rats there were decreased anionic GAG sites in the GBM. Enalapril treatment had a beneficial effect on the preservation of GAGs in the GBM of nephrotic PAN rats.

Example 2

Determination of the Effect of the RAS System on Proteoglycan Synthesis in Vitro The objective of these studies was to ascertain whether inhibition of RAS increased GAG synthesis in vitro in kidney mesangial cell cultures, endothelial cell cultures and chondrocyte cell cultures using a cell-associated GAG assay and radioactivity incorporation assay.

Materials and Methods

All tissue culture media and additives were from Biologic Industries, Beit Haemek, Israel. Enalaprilat (E) was a gift of MSD, Israel, and candesartan (C) was a gift of Astra Zeneka, Sweden.

Cells and Cell Lines

Rat mesangial cells (RMC): RMC derived from Sprague-Dawley rats (#ATCC-mesangial-CRL-2573) were cultured in DMEM supplemented with 15% fetal calf serum (FCS) and antibiotics, according to ATCC instructions. Mesangial cells are derived from the glomerular interstitium of the kidney and thus serve as a valuable tool for the analysis of the GBM.

Endothelial cells: Human umbilical vein endothelial cells (HUVEC) were isolated by collagenase treatment. Cultures were established in M-199 medium containing 10% FCS, 25 $\mu$l/ml endothelial mitogen (Biomedical Technologies, Mass., USA) and antibiotics. HUVEC were passaged by treatment with 0.25% trypsin/0.02% EDTA, and passages 2-3 were used for experiments.

Chondrocytes: Tissue bits from articular cartilage were incubated in-vitro and explant cell cultures were established as described [Nevo et al., 1972, Dev Biol 28: 219-228]. The cell cultures were assessed by immunohistochemistry.

Cell-Associated GAG Assays

Calorimetric assay: Cell-associated GAGs were isolated from RMC by cetylpyridinium chloride (CPC, Sigma) precipitation, as described by (Nevo et al., 1972). Briefly, cells were rendered quiescent in 2% FCS for 24 hours (i.e., starvation conditions), then incubated in DMEM for 36 hours with PAN 40 $\mu$g/ml (Sigma), in the presence of increasing doses of enalaprilat [(E), the active form of enalapril], according to the following protocol: control, PAN, PAN+E 200 $\mu$g/ml, PAN+E 400 $\mu$g/ml, PAN+E 800 $\mu$g/ml. Following thorough rinsing in PBS, RMC were harvested using 0.05% trypsin/EDTA. Following addition of a buffer containing 0.1 M sodium acetate, 0.005 M EDTA (Sigma), 0.005 M cysteine (Sigma), and 0.1% papain (Sigma), pH 5.4, the mixtures were incubated for 48 hours at 65° C. and dialyzed for 24 hours against distilled water. NaCl was added to the dialysate to a final concentration of 30 mM, and mixed well. GAGs were precipitated by the addition of CPC to a final concentration of 0.5% and the solution was incubated overnight at 37° C. The precipitate was collected by centrifugation, dissolved in 2 M $CaCl_2$, reprecipitated with ethanol:ether (2:1), collected by centrifugation and dried. GAGs were determined calorimetrically (uronic acid content×3.3=GAG content) using heparan sulfate as standard and expressed as $\mu$g GAGs/$10^6$ cells.

Radioactive assay ($^{35}$S labeling): Cells were grown to confluence, and were rendered quiescent in 2% FCS for 24 hours, following which they were transferred to serum-free medium plus one of the following additives: control, PAN 40 $\mu$g/ml, PAN+E 200 $\mu$g/ml, PAN+E 400 $\mu$g/ml, PAN+E 800 $\mu$g/ml, PAN+C$10^{-7}$M candesartan in the presence of 1 $\mu$Ci/ml $^{35}$S. Following 24 hours, medium was collected, cells were harvested by trypsinization, and aliquots obtained for cell and protein measurements. Cells were digested with papain as described, followed by extensive dialysis against water containing a non-radioactive sodium sulfate, until water contained less than 100 cpm/ml. Dialysate was transferred to Corex tubes and the same procedure was carried out as described for non-radioactive GAGs. Radioactivity was measured in a beta-counter.

Statistical analysis: Data are presented as mean±SE. In the in vivo study comparisons between groups were performed by use of one-way analysis of variance (ANOVA). The Mann-Whitney test was used for comparison in the in vitro study. Two-tailed $p<0.05$ was considered significant.

Results

Figure 4:
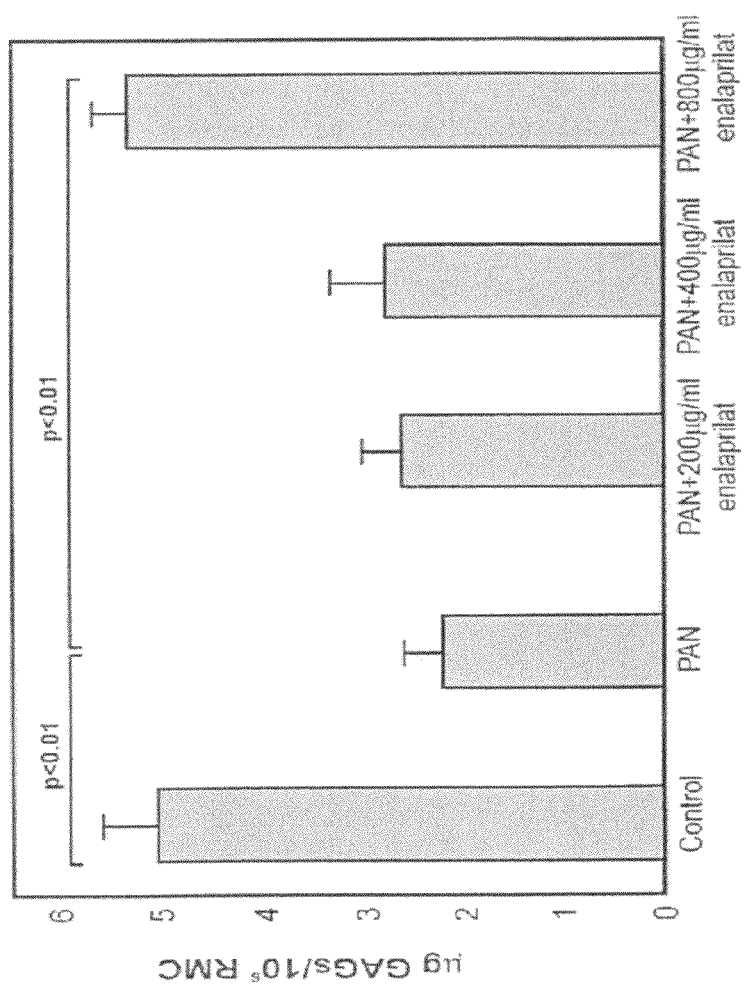
FIG. 4 is a bar graph illustrating the concentration of RMC-associated GAGs in culture. RMC were incubated with 40 μg/ml PAN, and increasing doses of enalapril. The results are depicted as μg GAGs/$10^6$ cells.

Calorimetric assay: PAN induced a significant decrease in cell-associated GAGs in RMC (FIG. 4). In the control group there were 5.03+0.6 $\mu$g GAGs/$10^6$ cells; in the PAN group there were 2.35±0.54 $\mu$g GAGs/106 cells, significantly less than in the control group ($p<0.01$). Addition of enalaprilat (E) to the culture medium led to a dose-dependent rise in GAG content. In PAN+E 200 $\mu$g/ml there were 2.43+0.42 $\mu$g GAGs/$10^6$ cells. In PAN+E 400 $\mu$g/ml there was a slight, but not significant rise to 2.8+0.65 $\mu$g GAGs/$10^6$ cells. In PAN+E 800 $\mu$g/ml there were 5.3±0.43 $\mu$g GAGs/$10^6$ cells, significantly higher than in the PAN group ($p<0.01$) and not different from the control group.

Radioactive Assay:

1. RMC

As shown in Table 3 below, PAN induced a significant decrease in cell-associated GAGs in RMC to 69% of control. Addition of enalaprilat 800 $\mu$g/ml to the culture medium raised GAG synthesis to 80%, whereas addition of candesartan $M^{-7}$ increased GAG synthesis to 102% of control values (all in the presence of PAN).

TABLE 3

| control | PAN 40 $\mu$g/ml | PAN + enalaprilat 800 $\mu$g/ml | PAN + candesartan $M^{-7}$ | PAN + candesartan $M^{-7}$ |
|---|---|---|---|---|
| 100% | 69 ± 4.84% | 80 ± 7.06% | 76 ± 6.2% | 102 ± 7.56% |

2. Endothelial Cells

PAN induced a significant decrease in cell associated GAGs to 81% of control, whereas the addition of enalaprilat 800 $\mu$g/ml raised GAG synthesis to 96%, and candesartan $M^7$ to 107% of control as shown in Table 4 below.

TABLE 4

| control | PAN 40 µg/ml | PAN + enalaprilat 800 µg/ml | PAN + candesartan M$^{-7}$ |
|---|---|---|---|
| 100% | 81% | 96% | 107% |

3. Chondrocytes

PAN induced a significant decrease in cell associated GAGs to 68% of control, whereas addition of enalaprilat 200 µg/ml raised GAG synthesis to 152% of control as shown in Table 5 below.

TABLE 5

|  | $^{35}$S-GAG cpm ± SD | % |
|---|---|---|
| Control culture | 6331 ± 1075 | 100 |
| In the presence of enalaprilat 200 µg/ml | 6820 ± 1651 | 108 |
| Pretreated with puromycin | 4333 ± 108 | 68 |
| Pretreatment with puromycin + enalaprilat 200 µg/ml | 9636 ± 1848 | 152 |

Conclusion

In conclusion, both ACE-inhibitors and angiotensin II receptor blockers were able to ameliorate the effects of puromycin induced decrease of GAGS by an activation of the synthesis of GAGs. This was shown in vivo in the rat kidney and was demonstrated in vitro in kidney, cartilage and endothelial cell cultures.

Example 3

Intra-Articular Administration of Ace-Inhibitors in an Animal Model of Osteoarthritis The objective of these studies was to ascertain whether intra-articular administration of an ACE inhibitor into an Osteoarthritic-induced rat may serve to retard or minimize the manifestations of osteoarthritis.

Materials and Methods

Osteoarthritis (OA) was induced in 32 rats using the model of partial meniscectomy of Rolli Moskowitz [Moskowitz, R W and Goldberg V M, J. Rheumatol. 1987 May; 14 Spec No:116-8; Moskowitz, R W et al., Ann Rheum Dis. 1981 December; 40(6):584-92]. The tissues of the control rats undergoing partial meniscectomy (8 rats) were immediately closed by suturing, while to the ACE-I treated group (24 rats), immediately following post partial meniscectomy, a composite gel containing ACE-I (5% captopril) was added prior to suturing the joint layers. After 6 weeks the animals were sacrificed. Prior to termination of the experiment a physical checkup ensured the degree of limping and movement limitation of the operated lower limb using an apparatus conducting a digital measurement of the degree of disability, translated to the pressure in grams activated by the operated limb, versus the healthy limb. Histological sections of the joint, femur and tibia, were prepared and stained with hematoxylin-eosin (H&E) as well as with Alcian blue at pH 2.5 and 1.0, and Masson's trichrome stain (Dako, Calif., U.S.A.). Together, these staining techniques assess proteoglycan content and extracellular matrix deposition.

Results

As illustrated in FIGS. 5A-B, control animals developed severe OA in both cartilage surfaces of the femor and tibia. Only a minor meniscal residue was left. Deep, fibrillations reaching the subchondral bone were seen. The articular cartilage was mainly acellular and depleted of most of its proteoglycans.

As illustrated in FIGS. 5C-D, animals treated with captopril, displayed an articular cartilage which is highly cellular, with a dense presentation of proteoglycans. There was only a mild initiation of OA, evident by minimal fibrillations and cell cloning.

Conclusion

Partial meniscectomy induces within weeks classical OA, with clear anatomical and histological signs. Intra-articular administration of ACE-I (captopril) slows down, and minimizes the OA manifestations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating osteoarthritis in a subject, the method comprising intra-articularly administering to a subject in need thereof a therapeutically effective amount of an agent capable of down-regulating activity or expression of a component of the renin-angiotensin system, wherein said agent is selected from the group consisting of an angiotensin converting enzyme (ACE) inhibitor, an AT1 receptor antagonist and a renin inhibitor, thereby treating osteoarthritis in the subject.

2. The method of claim 1, wherein the agent is an ACE inhibitor.

3. A method of treating osteoarthritis in a subject, the method consisting of intra-articularly administering to a subject in need thereof a therapeutically effective amount of an agent capable of down-regulating activity or expression of a component of the renin-angiotensin system, wherein said agent is selected from the group consisting of an angiotensin converting enzyme inhibitor an AT1 receptor antagonist and a renin inhibitor, thereby treating osteoarthritis in the subject.

4. The method of claim 3, wherein said angiotensin converting enzyme inhibitor is selected from the group consisting of AB-103, ancovenin, benazeprilat, BRL-36378, BW-A575C, CGS-13928C, CL242817, CV-5975, Equaten, EU4865, EU4867, EU-5476, foroxymithine, FPL 66564, FR-900456,Hoe-065, I5B2, indolapril, ketomethylureas, KRI-1177, KRI-1230, L681176, libenzapril, MCD, MDL-27088, MDL-27467A, moveltipril, MS-41, nicotianamine, pentopril, phenacein, pivopril, rentiapril, RG-5975, RG-6134, RG-6207, RGH0399, ROO-911, RS-10085-197, RS-2039, RS 5139, RS 86127, RU-44403, S-8308, SA-291, spiraprilat, SQ26900, SQ-28084, SQ-28370, SQ-28940, SQ-31440, Synecor, utibaprilat, WF-10129, Wy-44221, Wy-44655, Y-23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, 1(-(I-carboxy-6-(4-piperidinyl) hexyl)amino)-1-oxop-oropyl octahydro-1H-indole-2-carboxylicacid, Bioproject BP1.137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril.

5. The method of claim 3, wherein said AT1 receptor antagonist is selected from the group consisting of Saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP-48369, DA-2079, DE-3489, DuP-167, EXP-063, EXP-6155, EXP-6803, EXP-7711, EXP-9270, FK-739, HR-720, ICI-D6888, ICI-D7155, ICI-D8731, isoteoline, KRI-1177, L-158809, L-158978, L-159874, LR B087, LY-285434, LY-302289, LY-315995, RG-13647, RWJ-38970, RWJ-46458, S-8307, S-8308, saprisartan, saralasin, Sarmesin, WK-1360, X-6803, ZD-6888, ZD-7155, ZD-8731, BIBS39, CI-996, DMP-811, DuP-532, EXP-929, L-163017, LY-301875, XH-148, XR-510, zolasartan and PD-123319.

6. The method of claim 3, wherein said renin inhibitor is selected from the group consisting of enalkrein, RO 42-5892, A 65317, CP 80794, ES 1005, ES 8891, SQ 34017, CGP 29287, CGP 38560, SR 43845, U-71038, A 62198, A 64662, A-69729, FK 906 and FK 744.

7. The method of claim 3, wherein the agent is an ACE inhibitor.

* * * * *